(12) United States Patent
Neuberger

(10) Patent No.: US 9,149,335 B2
(45) Date of Patent: Oct. 6, 2015

(54) CONTACT FREE AND PERFORATION SAFE ENDOLUMINAL LASER TREATMENT DEVICE AND METHOD

(75) Inventor: Wolfgang Neuberger, Dubai (AE)

(73) Assignee: Biolitec Pharma Marketing Ltd, Labuan (MY)

( * ) Notice: Subject to any disclaimer, the term of this patent is extended or adjusted under 35 U.S.C. 154(b) by 38 days.

(21) Appl. No.: 12/951,617

(22) Filed: Nov. 22, 2010

(65) Prior Publication Data

US 2011/0130747 A1    Jun. 2, 2011

Related U.S. Application Data

(60) Provisional application No. 61/265,496, filed on Dec. 1, 2009.

(51) Int. Cl.
*A61B 18/18* (2006.01)
*A61B 18/24* (2006.01)

(52) U.S. Cl.
CPC ..................................... *A61B 18/24* (2013.01)

(58) Field of Classification Search
CPC ....... A61B 18/245; A61B 18/22; A61B 18/24
USPC .................................................. 606/8, 15, 16
See application file for complete search history.

(56) References Cited

U.S. PATENT DOCUMENTS

| | | | | |
|---|---|---|---|---|
| 4,134,641 | A | * | 1/1979 | Kao et al. .......................... 385/70 |
| 5,152,277 | A | * | 10/1992 | Honda et al. .................. 600/116 |
| 5,166,990 | A | * | 11/1992 | Riccitelli et al. ................ 385/12 |
| 5,281,212 | A | * | 1/1994 | Savage et al. .................... 606/15 |
| 5,454,807 | A | * | 10/1995 | Lennox et al. ................... 606/15 |
| 5,503,162 | A | * | 4/1996 | Athanasiou et al. .......... 600/587 |
| 5,628,744 | A | * | 5/1997 | Coleman et al. ................ 606/12 |
| 5,684,907 | A | * | 11/1997 | Sprehn et al. ................. 385/123 |
| 5,733,277 | A | * | 3/1998 | Pallarito ............................ 606/7 |
| 2004/0015159 | A1 | * | 1/2004 | Slater et al. ..................... 606/32 |
| 2005/0131400 | A1 | * | 6/2005 | Hennings et al. ............... 606/15 |
| 2008/0039693 | A1 | * | 2/2008 | Karasawa ...................... 600/175 |
| 2008/0281308 | A1 | * | 11/2008 | Neuberger et al. ............. 606/15 |

* cited by examiner

*Primary Examiner* — Lynsey Crandall
*Assistant Examiner* — Nathan J Jenness
(74) *Attorney, Agent, or Firm* — Bolesh J. Skutnik; BJ Associates

(57) ABSTRACT

A device and method for endovascular radiation therapy that prevents unwanted damage to blood vessels during treatment is described. The device is adapted to prevent the emission end of an energy delivery device from coming into contact with the wall of a blood vessel. The device is also adapted to sense the inputted radiation power and prevent irradiation above a preselected power or energy level. Both features serve to prevent radiation, having an overly high intensity or power density, from impacting the vessel wall and causing a puncture.

2 Claims, 2 Drawing Sheets

CONTACT FREE AND PERFORATION SAFE ENDOLUMINAL LASER TREATMENT DEVICE AND METHOD

DOMESTIC PRIORITY UNDER 35 USC 119(e)

This application claims the benefit of U.S. Provisional Application Ser. No. 61/265,496 by Wolfgang Neuberger, entitled "Contact free and perforation safe endoluminal laser treatment method and device" filed Dec. 1, 2009, which is incorporated by reference herein.

BACKGROUND OF THE INVENTION

1. Field of the Invention

Present invention relates to a device and method for treating venous disorders in general, and more particularly, an endovascular radiation therapy device with catheter to prevent damages in vascular wall.

2. Invention Disclosure Statement

Endovascular laser therapy is an effective and minimally invasive way to close diseased or abnormal blood vessels, and can be an effective alternative to more invasive treatments such as vein stripping, or chemical treatments. It can be effectively applied to treat various vascular abnormalities and diseases such as varicose veins.

Generally, endovascular laser therapy is accomplished by inserting a flexible optical fiber into a blood vessel and advancing it until the distal end (emission end) of the fiber is located near the area of the blood vessel that is to be closed. Typically, an introducer catheter/sheath is first inserted and advanced to a position near the desired location to be irradiated. This allows the optical fiber to be advanced into position while avoiding possible damage to the blood vessel or fiber during advancement.

Before irradiation, the optical fiber is positioned so that the distal end of the fiber is located in the introducer sheath at some short distance from the distal end of the sheath. The sheath is then partially withdrawn or the fiber is advanced to expose the fiber's distal end within the blood vessel. A radiation source such as a laser is then activated, and radiation is transmitted to the distal end of the fiber and is applied to the vessel wall. Generally, in order to close a desired length of the blood vessel, the optical fiber and sheath are slowly withdrawn while radiation is applied to the blood vessel.

Present methods and equipment for vein closing attempt to bring the vein walls into contact with the fiber optic device used. For example, in U.S. Pat. No. 6,398,777 by Navarro, a method for treating blood vessels using endovascular techniques to deliver laser energy is disclosed. Laser energy of 532 and 1064 nm is delivered into the vein using fiber optics and angiocatheter. Vein closing is achieved by contact of fiber with blood vessel wall. Such contact can result in vessel wall perforation.

Other state of the art treatments may allow for accidental contact between the fiber's distal end and the vessel wall. This can pose the risk of perforations if certain energy levels are exceeded or other unfortunate circumstances arise. Perforations result in bleeding into the surrounding tissue, causing post-treatment bruising and its associated discomfort.

There are numerous attempts to avoid contact with the vessel wall and regulate irradiation during intravascular laser treatments.

A balloon would be a prior art way to do this, but balloons are complex, prone to complication, and affect the amount of radiation incident on vessel wall. Also, a balloon may interfere with vein closure.

U.S. Pat. No. 5,167,686 by Wong discloses a catheter for delivering ablative radiant energy to a blood vessel to remove obstructive biological material. Radiation is applied in such a way that the energy density of the emitted beam drops sharply so that material beyond the working zone is not removed. This helps to avoid the risk of puncturing the blood vessel, as material is removed in limited layers. A fiber optic waveguide is extended through the lumen of the catheter, terminates in the catheter and is secured with an optical system located at the distal end of the catheter. The optical system both protects the optic fiber and shapes the beam to achieve the limited ablation desired.

U.S. Application No. 2007179486A1 by Welch et al. discloses a laser fiber optic for endovascular laser therapy; having a heat resistant insulated tip shield, covering the distal end of optic fiber. The insulative tip shield has echogenic qualities to increase ultrasound reflectivity. The distal tip of the optical fiber of ½ to 2 cm is not covered by protective shield. The chance of exposed tip getting carbonized when in contact with blood cells can cause thermal destruction to tissue, reduced output and also can damage the fiber tip.

U.S. Pat. Nos. 7,273,478 and 7,559,329 by Appling disclose an endovascular treatment device for use with an optical fiber, featuring a spacer to position the distal end of the fiber away from the inner wall of the blood vessel to evenly distribute radiation to avoid perforation or uneven closure. The spacer is initially in an "undeployed state" during insertion, and a "deployed state" where it positions the optical fiber for irradiation. The spacer may include a plurality of ribs which radially expand to position the fiber. The spacer may be incorporated into a catheter or attached to the optical fiber.

US Application 2008/0021527 A1 by Hennings et al. provides an apparatus and method for treatment of varicose veins. The improved method used reduces the amount of heat, induces coagulum at the fiber tip and prevents heat damage. This invention uses infrared radiation in the range of 1.2-2.7 μm to irradiate endothelial cells and collagen of the vein wall thus permanently occluding the vessel. A non-hemoglobin absorbing wavelength e.g. 1320 nm with higher energy per pulse is used to avoid formation on coagulum at the fiber tip. It also proposes the use of a silica clad fiber and a spacer to prevent coagulum at the fiber tip. Disadvantages to this invention include the need of movable means to center the fiber, which may cause improper position if the spacer does not deploy properly. Also, because the spacer is in contact with the vessel wall, it may become damaged or deformed while the fiber and spacer are withdrawn during irradiation.

It is an object of the present invention to provide a simplified device for endovascular radiation treatments that avoids puncturing the vessel wall by preventing contact between the emission means of an optical fiber and the vessel wall. The present invention addresses this need.

OBJECTIVES AND BRIEF SUMMARY OF THE INVENTION

It is an objective of the present invention to provide a device and method for endovascular radiation therapy that prevents the possibility of puncture or perforation of the vessel wall.

It is another objective of the present invention to provide a device for endovascular radiation therapy that prevents contact between the emission end of a light-delivery device and a vessel wall.

It is a further objective of the present invention to provide a device for endovascular radiation therapy that regulates the power of applied radiation.

It is still further objective of the present invention to provide a means of centering the fiber without coming in contact with vessel wall.

It is yet another objective of the present invention, to have sensing means to monitor and control emitted radiation to avoid emitting radiation having an excessively high power.

Briefly stated, the present invention discloses a device and method for endovascular radiation therapy that prevents unwanted damage to blood vessels during treatment. One feature is a means for preventing the emission end of a light delivery device from coming into contact with the wall of a blood vessel. This positioning means may be a distancing catheter or ring incorporated into a catheter. Another feature is a sensing means that senses the inputted radiation power and prevents irradiation above a preselected power or energy level. Both features serve to prevent radiation, having an overly high intensity or power density from impacting the vessel wall and causing a puncture.

The above and other objects, features and advantages of the present invention will become apparent from the following description read in conjunction with the accompanying drawings.

DETAILED DESCRIPTION OF PREFERRED EMBODIMENTS

Figure 1:
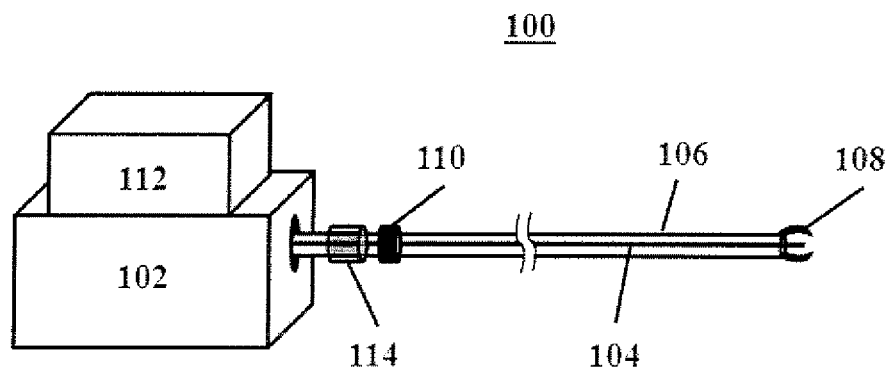
FIG. 1—shows an embodiment of an endo-luminous laser system for treating vein disorders comprising a laser source, an optical fiber, a flexible distancing catheter, securing means, a photodiode and a monitoring/controlling system.

The present invention is concerned with providing an improved endovascular radiation therapy device that reduces or eliminates the risk of puncture of a blood vessel wall due to irradiation. Such a puncture or breach of the vessel wall occurs when radiation of a sufficient high energy density impacts the wall. This may occur because the emission end of a radiation energy delivery device, typically an optical fiber, comes too close or comes in contact with the vessel wall. Increased energy density may also occur simply due to an accidental increase in the power emission of the radiation source. Either condition would result in unwanted damage to the blood vessel which could compromise the treatment or produce complications, due to bleeding for example.

Disclosed herein is an endovascular treatment device/system for minimally invasive irradiation of targeted blood vessels, having features designed to avoid accidentally over-irradiating the vessel wall, especially to avoid puncturing the blood vessel. The essential components of the system include an energy source for applying treatment radiation, an energy delivery device such as an optical fiber, one or more introducer sheaths/dilators, a distancing catheter, and an optional guidewire.

In one embodiment, the energy delivery device is an optical fiber. The optical fiber may be, for example, covered with a relatively thick polymer jacket. Typical fiber diameters are in the range of 600-microns. The optical fiber has a distal end which delivers light and a proximal end which is connected to a light source. The energy source is preferably a laser radiation source. Laser radiation sources may be of any type provided they emit the desired wavelength for a given treatment. The laser radiation sources may be solid state lasers or diode lasers, for example. Non coherent sources such as lamps and LED's can also be coupled to optical fibers through known focusing means.

In one embodiment, the distancing catheter is a centering catheter surrounding the introducer sheath. The centering catheter includes a means for securing the introducer sheath by preventing it from diverting radially and getting close to the vessel wall. The securing means are preferably positioned near the distal end of the catheter. The securing means may be of any shape, as long as it extends radially toward the center of the catheter and provides an opening of sufficiently small size to allow the introducer sheath to pass through but with very little divergence from the central portion of the catheter. The distal centering portion may be produced integrally with the catheter or may consist of a ring sized to a given introducer. The ring can then be secured in the catheter.

Another embodiment includes sensing means to allow the monitoring and control of emitted radiation to avoid excessive high power emission. The sensing means includes an optical sensor, a monitoring/controlling system; and means to transmit sensor information to the monitoring/controlling system. In one embodiment the optical sensor is a photodiode which can be present at the proximal end of the fiber accepting radiation reflected off a vein wall back through the fiber to the sensor, or at the distal end of the fiber with means to transfer signal back to controlling means. The sensing means (system), which can preferably be calibrated prior to treatment, feeds back a portion of the treatment radiation and compares the power reading to a previously entered maximum. If the power reading is at or above a given maximum, the monitoring/control system can alert the user or automatically shut off the radiation source. In this manner, unwanted damage or breach of the vessel wall can be avoided. In another embodiment, preferably two maximum values are set; one is set manually by the doctor according to the vessel to be treated and the other is set automatically by the endovascular radiation device.

In a preferred embodiment, both the centering catheter and the sensing means are incorporated into the endovascular treatment device/system, so that both the proper emitted power can be maintained and the emission end of the light delivery device can be prevented from contacting the wall of the blood vessel.

In one embodiment, the method for treating vascular disorders without causing accidental puncture or perforation to a vessel wail includes the steps of 1) selecting a vein for treatment; 2) positioning a light delivery device in a distancing catheter; 3) securing the light delivery device in the distancing catheter using securing means; 4) connecting the light delivery device at its proximal end to a laser source; 5) inserting the introducer/dilator sheath and advancing it to desired position; 6) inserting the coupled light delivery device and distancing catheter into the vein to be treated; 7) withdrawing the introducer/dilator sheath; 7) positioning the coupled light delivery device and distancing catheter in the vessel without contacting vein walls; and 8) irradiating the vein to be treated while the light delivery device and the distancing catheter are jointly withdrawn to cause the closure of said selected vein.

In another embodiment, the method for treating vascular disorders without causing incidental puncture or perforation to a vessel wall includes the steps of 1) selecting and marking a vein for treatment; 2) positioning a light delivery device in a distancing catheter; 3) securing the light delivery device in the distancing catheter using securing means; 4) connecting the light delivery device at its proximal end to a laser source; 5) puncturing the vein to be treated and inserting guide wire; 6) inserting catheter and removing guide wire; 7) inserting the coupled light delivery device and distancing catheter into the vein to be treated; 8) removing catheter: 9) positioning the coupled light delivery device and distancing catheter in the vessel without contacting vein walls; and 10) irradiating the vein to be treated while the light delivery device and the distancing catheter are jointly withdrawn to effect the closure of said selected vein.

The present invention is further illustrated by the following examples, but is not limited thereby.

EXAMPLE 1

In one example the method of the present invention is used to treat incompetent great saphenous vein (GSV), With the aid of duplex ultrasound scanning incompetent portions of the vein to be treated are identified and marked. Then, an assembly is prepared by inserting an optical fiber in the distancing catheter in a way that the tip of the optical fiber exceeds approximately 1.5 cm. This position is marked with a locking system that allows appropriate assembly. Where appropriate, different methods can be used to avoid/minimize a patient's pain or discomfort, including spinal or general anesthesia, femoral nerve block (to achieve a sensorial block) or intravenous dripping anesthesia. In case spinal or general anesthesia is chosen it is administered at this stage. If femoral nerve block is preferred, the nerve block is also accomplished before starting the procedure by injecting an appropriate amount of local anesthetic in the vicinity of femoral nerve close to the femoral artery under ultrasound control. Then, a percutaneous entry point is chosen and with the use of ultrasound guidance the GSV is punctured with a 18G needle. A 0.035 guide wire is advanced up to the desired position and then the needle is removed. Next, a 5 Fr dilator-catheter set is placed over the wire. Afterwards, the guide wire and the dilator are withdrawn and the assembly, comprising a 600 .mu.m optical fiber and a distancing catheter, is inserted in the 5 Fr catheter. The 5 Fr catheter is withdrawn while maintaining the optical fiber/distancing catheter assembly approximately 2 cm away from the sapheno-femoral junction (SFJ), checking the correct position with ultrasound guidance. In case intravenous dripping anesthesia is chosen, the solution containing the anesthetic is delivered through the open conduit formed between the optical fiber and the distancing catheter, with the aid of a stopcock placed at the proximal end of the distancing catheter. Then, laser energy is delivered with the aid of a 980 nm diode laser (ELVeS.RTM., Endovenous Laser Vein System, diode laser Ceralas D25—biolitec Inc., East Longmeadow, Mass.), while the optical fiber/distancing catheter assembly is pulled back. The pull back speed is adjusted according to the linear endovenous energy density (LEER) that has to be achieved to properly treat the vein, which depends on the diameter of the vein and its distance to the skin. Postoperatively compressive stockings, class II (30-40 mm Hg), must be worn for at least one week.

EXAMPLE 2

Alternatively, instead of using a dilator-catheter set and an optical fiber/distancing catheter assembly, only three elements, the optical fiber, the dilator and the distancing catheter can be used. In this case, firstly the incompetent portions of the vein to be treated are identified and marked under ultrasound guidance. Then, a conical dilator is inserted into the distancing catheter until the end part of the dilator protrudes from the distancing catheter by about 2 cm. Then, local intradermal anesthesia is administered at the point of percutaneous or surgical entry. By using a 19G needle and under ultrasound guidance, a micro-incision is made with the tip of a blade and then the internal saphenous vein is punctured. Next, a guide wire is introduced into the vein up to the saphenofemoral junction, monitoring progress with ultrasound guidance. Next, the needle is removed and the dilator-distancing catheter assembly is fit onto the guide wire and is advanced up to the sapheno-femoral junction. After that, the conical dilator and the guide wire are withdrawn while the distancing catheter is left in place and 2 cm away from the sapheno-femoral junction, checking the correct position with ultrasound guidance. Subsequently, the proximal end of a 600 µm optical fiber is connected to a diode laser of 1470 nm (ELVeS® PL, Endovenous Laser Vein System, diode laser Ceralas E15— biolitec Inc., East Longmeadow, Mass.) and the distal end of the optical fiber is introduced into the distancing catheter. Optical fiber's tip is advanced until matching the distancing catheter's tip. Then, the catheter is withdrawn 2 cm, leaving the tip of the optical fiber exposed. According to diameter of the saphenous vein and its depth below the skin, the laser parameters are set. Usually, 30-80 J of energy for each cm of vein treated are needed to treat the vein. Finally, laser radiation is applied while withdrawing the fiber-distancing catheter assembly with the appropriate pull back speed. Postoperatively compressive stockings, class II (30-40 mm Hg), must be worn for at least one week.

EXAMPLE 3

In another example, endo-luminous laser system 100 for treating vein disorders is illustrated in FIG. 1. Endo-luminous laser system 100 comprises laser source 102, optical fiber 104, flexible distancing catheter 106, securing means 108, photodiode 110 and monitoring/controlling system 112. Optical fiber 104 having a diameter of 600 microns is introduced into flexible distancing catheter 106; which can center optical fiber 104 to avoid contact with vein walls. To maintain appropriate relative position of optical fiber 104 inside flexible distancing catheter 106 lock system 114 is used. Securing means 108 at the distal end of flexible distancing catheter 106 avoid contact with vein walls. Photodiode 110 is placed at the proximal end of optical fiber 104. Monitoring/controlling means are used to transmit sensor information regarding the laser radiation power delivered to the monitoring/controlling system 112, to avoid high power damage to the vessel walls. The radiation reflected from the vein wall is transmitted to monitoring/controlling system 112 which controls the power output intensity and thus prevents excess irradiation being delivered to the vein walls.

EXAMPLE 4

Figure 2A:
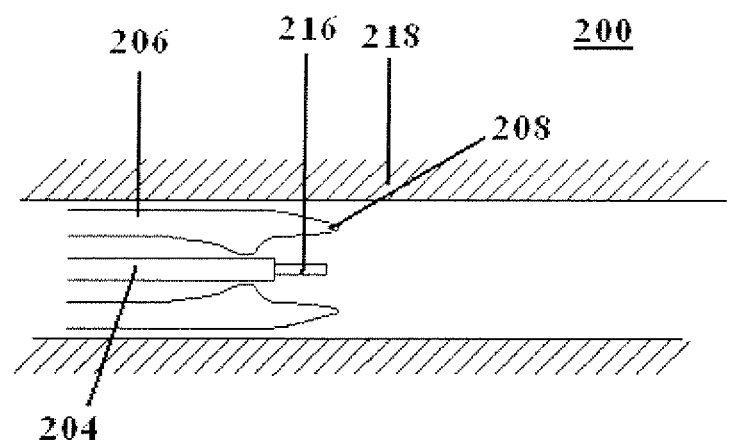
FIGS. 2a and 2b—illustrate an embodiment to center the light delivery device and to avoid contact with the wall of the blood vessel.
Figure 2B:
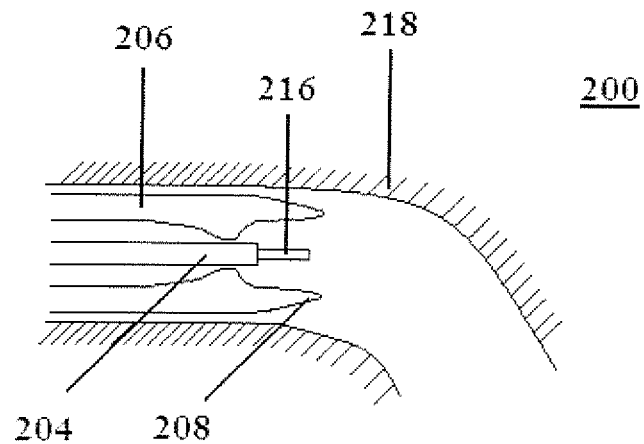

FIGS. 2a and 2b illustrate a preferred embodiment of the present invention featuring means to center the light delivery device and avoid contact with blood vessel walls. To achieve this, endo-luminous laser system 200 comprises flexible centering catheter 206 with distal centering portion 208 for protecting irradiation fiber tip 216 of optical fiber 204 from coming in direct contact with vessel wall 218. Flexible centering catheter 206 is designed for securing the sheath by preventing it from diverting radially and getting near to the vessel wall. Described centering is achieved in straight segments of vein as well as in curved segments as depicted in 2a and 2b respectively. The distal portion of the catheter can be shaped as shown in FIG. 2 but is not limited, and can include other shapes, which achieve its main purpose.

EXAMPLE 5

Figure 3:
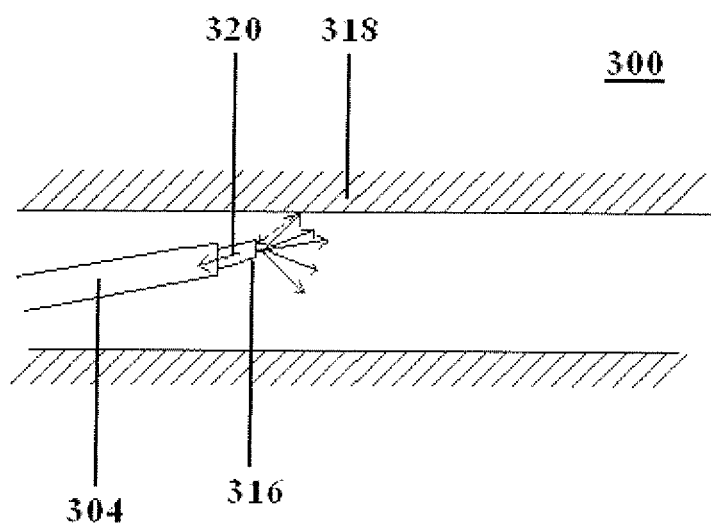
FIG. 3—illustrates an embodiment wherein a sensor system is employed to warn of proximity of a vein wall as fiber is deployed under guiding light.

FIG. 3 illustrates yet another embodiment of the endoluminous irradiation system 300 of the present invention. It is provided with a sensing and monitoring system at the proximal end (not shown) which can detect excessive high power transmission striking vessel wall 318 by detecting reflected power 320. Tracking reflected power 320 can also get help in determining the distance of optical fiber tip 316 from vessel wall 318 and thus help in center positioning of the optical fiber 304 to perform a contact free irradiation. In a preferred embodiment, after sensing the temperature and/or the intensity of light reflexion, the intensity of the laser power is adjusted automatically by the laser device. Alternatively, system suggests to the doctor the appropriate laser power to be used. In this way, the risk of perforating the vein in diminished.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. An endovascular radiation device for treating vascular disorders without causing puncture or perforation to the vessel wall consisting of:
   a distancing catheter and
   an optical fiber inside of and coaxial with the distancing catheter, connected at its proximal end to an energy source and configured to deliver energy at its distal end;
   the distancing catheter having an open-ended flexible catheter tip comprising a distal end defining an open lumen and a securing ring integrally formed in the open-ended flexible catheter tip or secured to an inner surface of the open-ended flexible catheter tip, the securing ring protruding radially from the inner surface of the open-ended flexible catheter tip toward the center of the open-ended flexible catheter tip, the securing ring being configured to secure and center the optical fiber inside the open-ended flexible catheter tip to prevent the optical fiber from diverting radially toward a vessel wall or beyond the distal end of the open-ended flexible catheter tip as the distal end of the optical fiber extends into the open lumen of the open-ended flexible catheter tip without contacting the open-ended flexible catheter tip on the distal side of the securing ring.

2. The device according to claim 1, wherein said energy source is a laser source.

* * * * *